United States Patent [19]

Das

[11] Patent Number: 4,611,007
[45] Date of Patent: Sep. 9, 1986

[54] 7-OXABICYCLOHEPTANE SUBSTITUTED PROSTAGLANDIN ANALOGS USEFUL IN THE TREATMENT OF THROMBOTIC DISEASE

[75] Inventor: Jagabandhu Das, Plainsboro, N.J.

[73] Assignee: E. R. Squibb & Sons, Inc., Princeton, N.J.

[21] Appl. No.: 725,976

[22] Filed: Apr. 22, 1985

[51] Int. Cl.$^4$ ............... A61K 31/34; A61K 31/557; C07D 307/00
[52] U.S. Cl. ..................... 514/469; 549/463
[58] Field of Search ................ 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,537,981 | 8/1985 | Snitman et al. | 549/463 |

FOREIGN PATENT DOCUMENTS 0043292  8/1982  European Pat. Off. .
2039909  8/1980  United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted prostaglandin analogs are provided having the structural formula

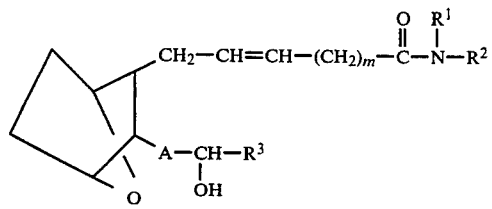

and including all stereoisomers thereof.

The compounds are cardiovascular agents useful, for example, in the treatment of thrombotic disease and as inhibitors of 5-lipoxygenase enzyme.

12 Claims, No Drawings

7-OXABICYCLOHEPTANE SUBSTITUTED PROSTAGLANDIN ANALOGS USEFUL IN THE TREATMENT OF THROMBOTIC DISEASE

DESCRIPTION OF THE INVENTION

The present invention relates to 7-oxabicycloheptane substituted prostaglandin analogs which are cardiovascular agents useful, for example, in the treatment of thrombotic disease and which are inhibitors of $\Delta^5$-lipoxygenase and prostaglandin and leukotriene biosynthesis and as such are useful, for example, as anti-allergy and anti-inflammatory agents. These compounds have the structural formula

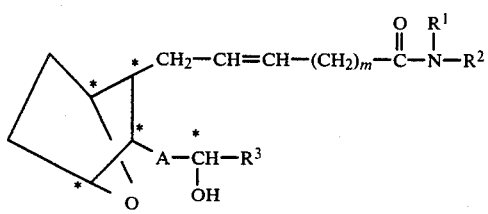

I and including all stereoisomers thereof, wherein m is 1 to 5; A is —CH=CH— or —(CH$_2$)$_2$—; R$^1$ is hydrogen or lower alkyl, R$^2$ is hydroxy, alkoxy or hydroxyphenyl; and R$^3$ is lower alkyl, aryl, aralkyl, cycloalkyl, cycloalkylalkyl, lower alkenyl or lower alkynyl.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups substituted with hydroxy; alkylamino; alkanoylamino; arylcarbonylamino; nitro; cyano; thiol; alkylthiohalo; such as F, Br, Cl or I or CF$_3$, alkoxy; aryl; alkyl-aryl; haloaryl; a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups; lower alkoxy groups; 1 or 2 hydroxyl groups; 1 or 2 alkylamino groups; 1 or 2 alkanoylamino groups; 1 or 2 arylcarbonylamino groups; 1 or 2 amino groups; 1 or 2 nitro groups; 1 or 2 cyano groups; 1 or 2 thiol groups; and/or 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl naphthyl may be 1 or 2 lower alkyl groups, halogens (Cl, Br or F); 1 or 2 hydroxy groups; 1 or 2 lower alkoxy groups; 1 or 2 nitro groups; 1 or 2 cyano groups; 1 or 2 thiol groups; and/or 1 or 2 alkylthio groups. In addition, the aryl group may be substituted with 1 or 2 NR$^2$R$^3$, groups or 1 or 2

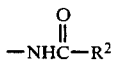

groups, wherein R$^2$ and R$^3$ are the same or different and can by hydrogen, lower alkyl or aryl.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The term "halogen" or "halo" as used herein by itself or as part of another group refers to chlorine, bromine, fluorine or iodine, with chlorine being preferred.

The term "hydroxyphenyl" as used herein refers to 2-hydroxyphenyl, 3-hydroxyphenyl, or 4-hydroxyphenyl.

The term "(CH$_2$)$_m$" includes a straight or branched chain radical having 1 to 5 carbons in the normal chain and may contain one or more lower alkyl and/or halo substituents. Examples of (CH$_2$)$_m$ groups include

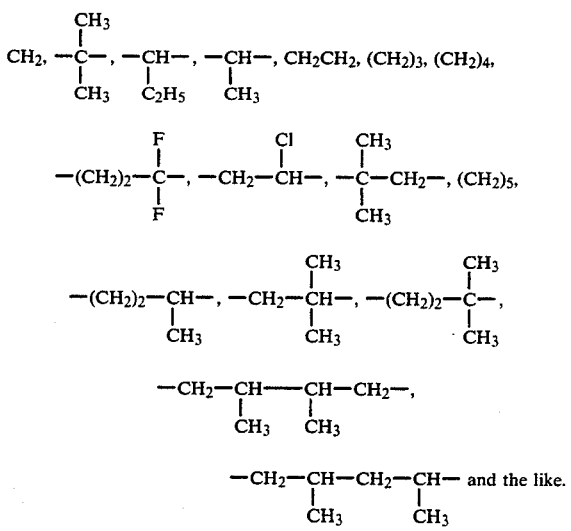

Preferred are those compounds of formula I wherein A is —CH=CH— or —CH$_2$—CH$_2$—, m is 2 to 4, R$^1$ is H or methyl and R$^2$ is OH or hydroxyphenyl, and R$^3$ is lower alkyl, such as hexyl, aryl, such as phenyl, or aralkyl such as benzyl and benzylmethyl.

The various compounds of the invention may be prepared as outlined below.

The starting tetrahydropyranyl ether VIII may be prepared according to the following reaction sequence.
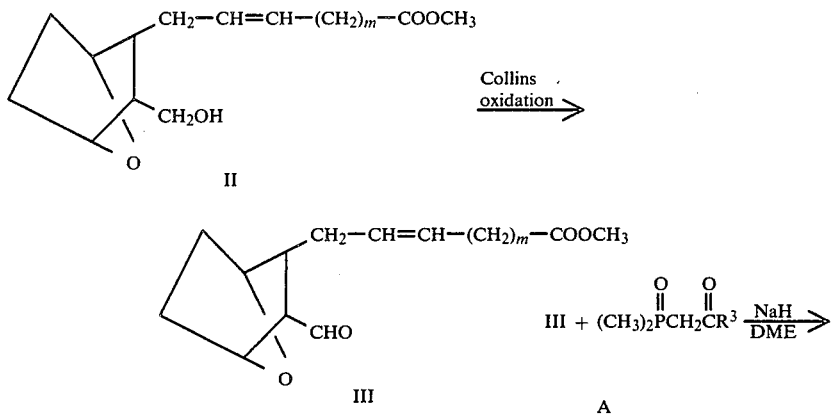
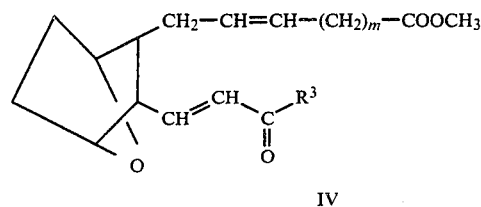
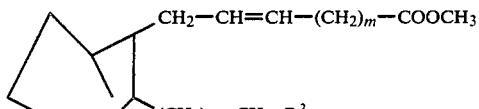
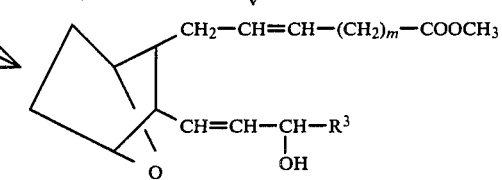
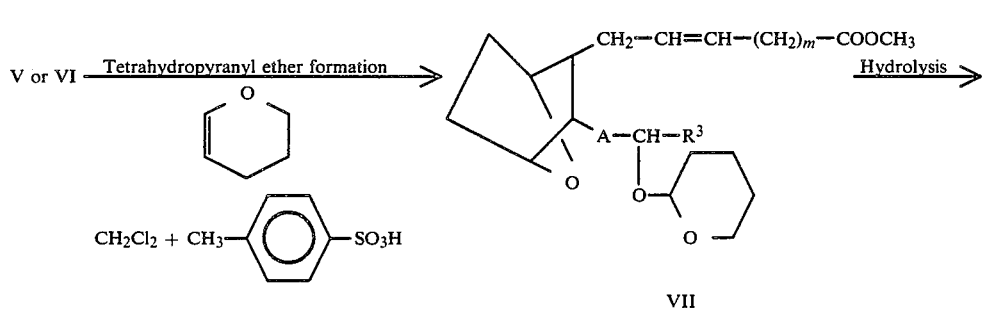

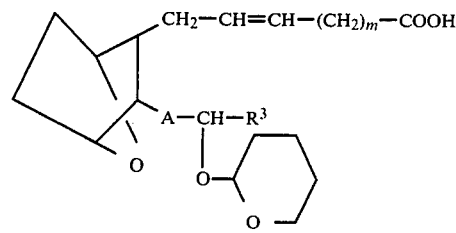

VIII

The starting lowr alkyl ester containing the hydroxymethyl group (that is, compound II) (prepared as described in U.S. Pat. No. 4,143,054) is used to the form the aldehyde III. Thus, to form aldehyde III, compound II is subjected to a Collins oxidation, for example, by reacting II with chromium oxide in pyridine.

Aldehyde III of the structure

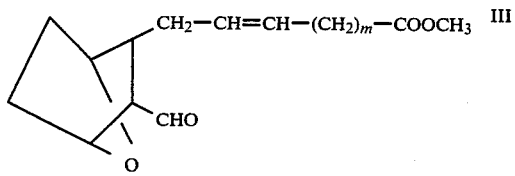

is reacted with a dialkoxy phosphonate, such as of the structure

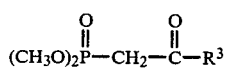

employing a molar ratio of III:A of within the range of from about 1:1 to about 0.5:1, under basic conditions, such as in the presence of sodium hydride or lithium diisopropylamide and an inert organic solvent, such as dimethoxyethane (DME), ether, tetrahydrofuran or toluene to form a compound of the structure

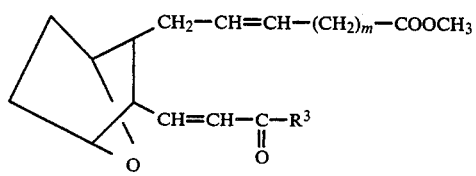

Compund IV may then be reduced by two different ways as outlined above to form compounds V or VI

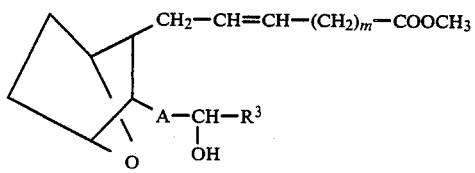

V - A is $(CH_2)_2$
VI - A is $-CH=CH-$ or compounds of the general formula IVA

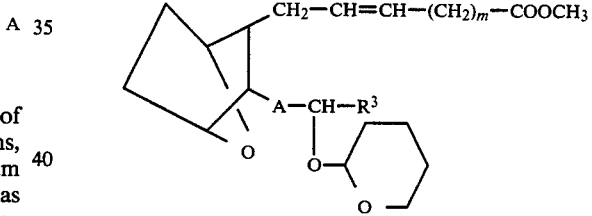

The allylic alcohol IVA is made to undergo tetrahydropyranyl ether formation by reacting allylic alcohol IVA with dihydropyran in the presence of an inert organic solvent such as methylene chloride or ether and catalytic amount of p-toluene sulfonic acid at reduced temperatures of from about 0° C. to about 10° C., to form the tetrahydropyranyl ether of formula VII

VII

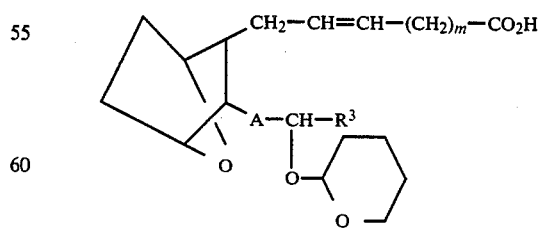

The corresponding acid VIII is prepared by hydrolyzing tetrahydropyranyl ether VII by treatment with a base such as lithium hydroxide, potassium carbonate or sodium hydroxide in the presence of an inert solvent such as tetrahydrofuran, methanol or dimethoxyethane-water to form the corresponding alkali metal salt which is then treated with acid such as HCl to form the acid compound VIII

VIII

Compounds of formula I of the invention wherein $R^1$ is hydrogen and $R^2$ is hydroxy may be prepared by subjecting acid VIII (wherein A is $CH=CH$) to a coupling reaction by reacting acid VIII with an O-protected hydroxyl amine of the structure B NH₂—OProtecting group    B (wherein the protecting group is benzyl, tetrahydropyranyl, methylthiomethyl or methoxymethyl)
in the presence of an activating catalyst such as 1-hydroxybenzotriazole (HOBT) and a coupling reagent such as N,N'-dicyclohexylcarbodiimide (DCC) in the presence of an inert organic solvent such as methylene chloride to form protected compound IX

IX

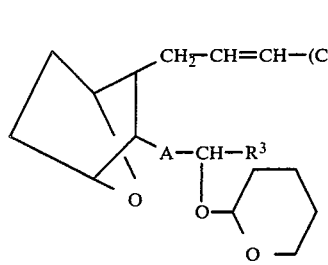

(A is CH=CH or (CH₂)₂)
Compound IX is hydrolyzed by treatment with strong acid such as HCl, Amberlyst resin or acetic acid in the presence of dimethoxyethane, tetrahydrofuran or other inert solvent to form the hydroxyamine compound of the invention IA

IA

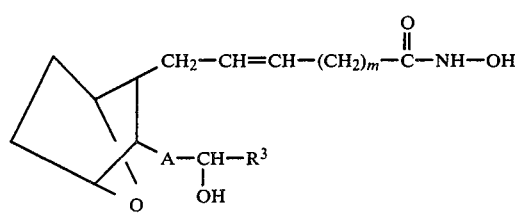

(wherein A is —CH=CH— or (CH₂)₂)

Compounds of formula I of the invention wherein $R^1$ is lower alkyl and $R^2$ is hydroxy may be prepared by treating compound IX with sodium hydride or other base and an alkyl halide C R¹Hal    C (wherein $R^1$ is lower alkyl)
in the presence of an inert solvent such as tetrahydrofuran to form the protected compound X

X

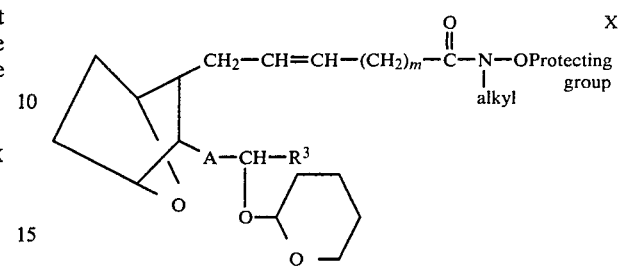

which is then hydrolyzed with Amberlyst resin (in the presence of methanol) or other strong acid to form compounds of the invention IB

IB

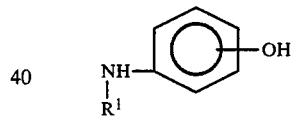

Compounds of formula I wherein $R^1$ is H or lower alkyl and $R^2$ is hydroxyphenyl may be prepared by treating acid VIII with an activating catalyst such as 1-hydroxybenzotriazole and a coupling reagent such as N,N'-dicyclohexylcarbodiimide and aminophenol D

D

NH—⟨phenyl⟩—OH
|
R¹ in the presence of methylene chloride solvent to form the amide XI

XI

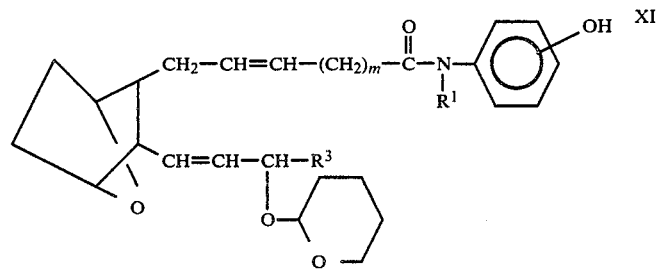

which is then hydrolyzed as described hereinbefore, for example, using Amberlyst resin in the presence of methanol to form compounds of the invention IC

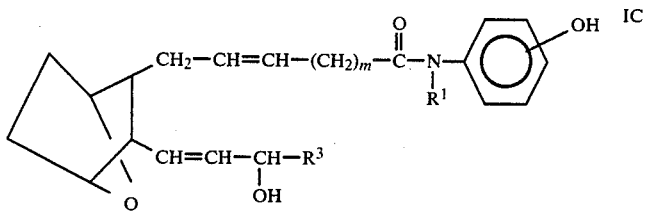

Compounds of the invention wherein $R^1$ is H or lower alkyl and $R^2$ is lower alkoxy may be prepared by reacting acid VIII with an amine of the structure E

```
NH—Oalkyl        E
|
R²
``` in the presence of an activating catalyst such as 1-hydroxybenzotriazole and a coupling reagent such as N,N'-dicyclohexylcarbodiimide and an inert solvent such as methylene chloride to form XII

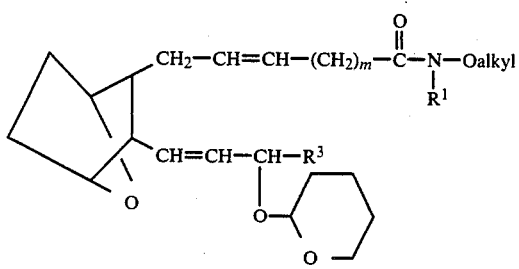

which is then hydrolyzed as described hereinbefore to form compunds of the invention ID

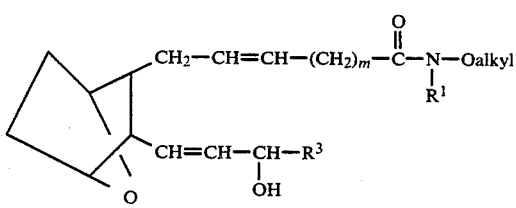

The compounds of this invention have five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

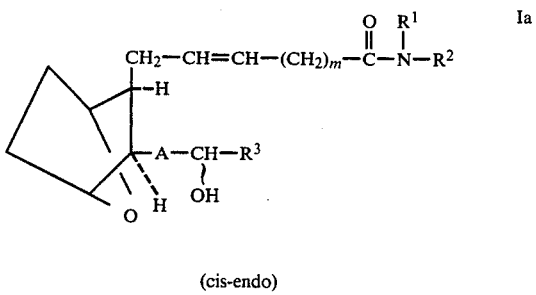

(cis-endo)

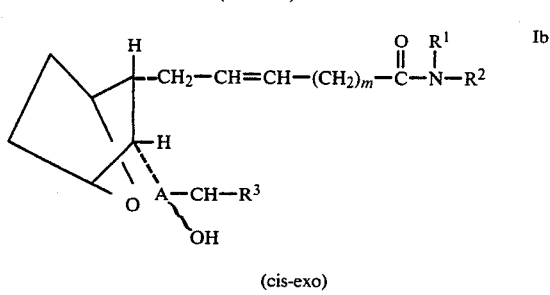

(cis-exo)

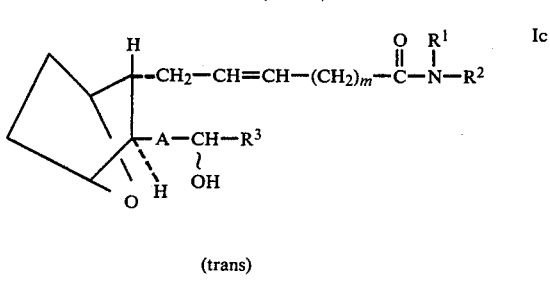

(trans)

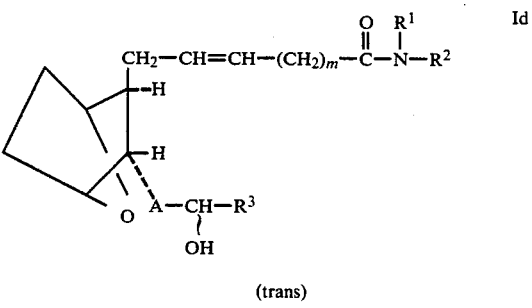

(trans)

The wavy line ( $\wr$ ) in the above formulae indicates that the hydroxy group in each of the compounds of formulae Ia-Id is either $R(\beta)$ or $S(\alpha)$.

The nucleus in each of the compounds of the invention is depicted as

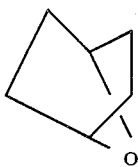

for matter of convenience; it will also be appreciated that the nucleus in the compounds of the invention may be depicted as

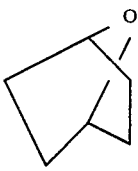

The compounds of the invention are $\Delta^5$-lipoxygenase inhibitors and prevent prostaglandin and leukotriene $C_4$ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma. In addition, the compounds of the invention are useful as antipsoriatic agents.

The compounds of the invention are useful as antiinflammatory agents in the manner of indomethacin and phenylbutazone as indicated by carragenin-induced edema in the rat [Ref: Winter et al, J. Pharmacol, Exp. Ther. 141:369, 1963] and they may be used to decrease joint swelling, tenderness, pain and stiffness in conditions such as rheumatoid arthritis.

The compounds of this invention are also cardiovascular agents useful as platelet aggregation inhibitors, such as inhibiting arachidonic acid-induced platelet aggregation (e.g., for treatment of thrombotic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of mycardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1S-[1α,2β(5Z), 3β(1E,3R,4S),4α]]-N-Hydroxy-7-[3-(3-hydroxy-4-phenyl-1-pentenyl)-7-oxabicyclo[2.2.1]-hept-2-yl]-5-heptenamide

A.

[1α,2β(Z),3β(1E),4α]-7-[3-(3-Hydroxy-4-phenyl-1-pentenyl)-7-oxabicyclo[2.2.1]hept-2-yl]-5-heptenoic acid, methyl ester (1) (+) Methyl 2-phenylpropionate (+) 2-Phenylpropionic acid (8.4 g, 56 mmol) in methanol (180 ml) and concentrated $H_2SO_4$ (2 ml) were heated at reflux for 4 hours. The reaction was cooled down to room temperature and concentrated in vacuo (~100 ml). The products were extracted with $Et_2O$ (150 ml×3), which was washed with saturated $NaHCO_3$, $H_2O$ and dried over $MgSO_4$. Filtration and evaporation of solvent yielded a yellow oil (8.9 g), which was distilled to give (+) methyl 2-phenylpropionate as a colorless oil (8.34 g, 51 mmol, 91%, b.p. 73° C./1.5 mm Hg), $[\alpha]^D = +111°$ (c=2, toluene).

(2) (+) 2-Oxo-3-phenylbutyl dimethyl phosphonate n-Butyllithium (1.6M, 62.5 ml, 100 mmol) was added dropwise to a magnetically stirred solution of dimethylmethyl phosphonate (12.4 g, 100 mmol) in THF (90 ml) at −78° C. Stirring was continued for 30 minutes at −78° C. Then ester from Part A (8.2 g, 50 mmol) was added dropwise to give a yellow colored solution. After 3 hours stirring at −78° C., the reaction was warmed to room temperature and stirred for 1 hour. The reaction was quenched by addition of acetic acid to pH 5~6. The solvent was removed in vacuo and $H_2O$ (100 ml) was added. The products were extracted with $CH_2Cl_2$ (100 ml×3), which was washed with saturated $NaHCO_3$, $H_2O$ and dried over $MgSO_4$. Filtration and evaporation of solvent left a yellow oil. This was fractionated to give (+)2-oxo-3-phenylbutyl dimethyl phosphonate (8.1 g, 31.6 mmol, 63%, b.p. 142°–144°/0.2 mm Hg), $[\alpha]^D = +235°$ (c=2, toluene).

(3)

[1α,2β(Z),3β(1E,4S),4α]-7-[3-(3-Oxo-4-phenyl-1-pentenyl)-7-oxabicyclo[2.2.1]-hept-2-yl]-5-heptenoic acid, methyl ester Sodium hydride (201 mg of 50% in mineral oil, 4.18 mmol) was suspended in distilled dimethoxyethane (70 ml) in an argon atmosphere and treated with a solution of Part A(2) phosphonate (1.45 g, 4.7 mmol) in DME (10 ml). The mixture was stirred at room temperature 90 minutes. A solution of (+)-[1α,2β(Z),3β,4α]-7-[3-formyl-7-oxabicyclo[2.2.1]-hept-2-yl]-5-heptenoic acid, methyl ester (prepared as described in U.S. Pat. No. 4,143,054) (1.031 g, 3.8 mmol) in DME (5 ml) was then added and the mixture was stirred overnight at room temperature. The reaction was quenched by adding glacial acetic acid (0.5 ml) and the solvent was removed in vacuo. Ether and saturated NaHCO$_3$ were added and the layers were separated. The ether layer was washed once with saturated NaHCO$_3$ solution, dried over MgSO$_4$, filtered and taken to dryness in vacuo leaving a viscous oil. This was chromatographed on silica gel 60 (110 g), eluting with ether-pet ether (2:3) to give 992 mg (66%) of title A (3) compound as an oil. A faster moving material (98 mg, 6.5%) was also isolated and identified by $^1$H NMR as the cis double bond isomer.

(4)
[1α,2β(Z),3β(1E),4α]-7-[3-(3-Hydroxy-4-phenyl-1-pentenyl)-7-oxabicyclo[2.2.1]hept-2-yl]-5-heptenoic acid, methyl ester Title compound from Part A (3) (0.99 g, 2.49 mmol) and CeCl$_3$·7.6H$_2$O (0.954 g, 2.49 mmol) were dissolved in methanol (25 ml) and THF (2 ml). The solution was cooled in an ice bath and NaBH$_4$ (94.1 mg, 2.5 mmol) was added portionwise in 30 seconds. The ice bath was removed and the mixture was stirred 10 minutes, then poured into saturated NH$_4$Cl solution (200 ml). The product was extracted into ethyl acetate (5×50 ml). The combined ethyl acetate extracts were dried (MgSO$_4$), filtered, and freed of solvent in vacuo to give a viscous oil (0.953 g). This was chromatographed on silica gel 60 (60 g) eluting with ether-pet ether (3:2) to give 616 mg of nearly clean faster moving isomer and 150 mg (15%) of slower moving isomer. TLC's silica gel; Et$_2$O-pet ether 3:2; vanillin R$_f$'s 0.35 and 0.25. The faster moving isomer was rechromatographed eluting with the same solvent to give 605 mg (61%) of title A compound.

B.
[1α,2β(Z),3β(1E,4S),4α]-7-[3-(3-Tetrahydropyranyloxy-4-phenyl-1-pentenyl)-7-oxabicyclo[2.2.1]hept-2-yl]-5-heptenoic acid, methyl ester To a solution of 2.16 g of title A chiral allylic alcohol (5.4 mmole) in 20 ml of dry methylene chloride was added with stirring a catalytic amount of p-toluene sulfonic acid, followed by 750 μl of dihydropyran (8.33 mmole) at 0°–5° C. The reaction mixture was stirred at 0°–5° C. for 40 minutes whereupon it was washed with aqueous sodium bicarbonate solution. The methylene chloride layer was separated and the aqueous layer was extracted with ether. The combined organic extract was dried over anhydrous magnesium sulfate and concentrated under reduced pressure. Purification by flash chromatography on a silica gel column gate 2.43 g of desired title THP-ether (eluting solvent 10–15% ethyl acetate in hexane).

C.
[1α,2β(Z),3β(1E,4S),4α]-7-[3-(3-Tetrahydropyranyloxy-4-phenyl-1-pentenyl)-7-oxabicyclo[2.2.1]hept-2-yl]-5-heptenoic acid To a solution of 11.78 g of Part B tetrahydropyranyl ester (24.3 mmole) in 100 ml of distilled THF (tetrahydrofuran) was added with stirring 50 ml of a 1N aqueous lithium hydroxide solution (50 mmole). The reaction mixture was allowed to stir at room temperature under an argon atmosphere for 24 hours, whereupon it was placed in an ice-water bath and carefully acidified to pH 4.5 by dropwise addition of a 1N aqueous hydrochloric acid solution. The THF layer was separated and the aqueous layer was extracted several times with ether. The combined ether and THF extract was washed with saturated salt solution, dried over anhydrous magnesium sulfate and finally was concentrated under reduced pressure to obtain 11.27 g of desired title acid as a colorless viscous oil.

D.
[1α,2β(Z),3β(1E,4S),4α]-7-[3-(3-Tetrahydropyranyloxy-4-phenyl-1-pentenyl)-N-tetrahydropyranyloxy-7-oxabicyclo[2.2.1]hept-2-yl]-5-heptenamide To a solution of 180 mg of Part C acid compound (0.38 mmol) in 2 ml of CH$_2$Cl$_2$ at 25° C. was added 65 mg of 1-hydroxybenzotriazole (0.46 mmole, 1.2 equiv.) and 93.6 mg of 1,3-dicyclohexylcarbodiimide (0.46 mmole, 1.2 equiv.). After stirring at 25° C. for 1 hour, 90 mg of O-tetrahydropyranyl hydroxylamine (0.76 mmole, 2 equiv.) was added and the stirring was continued for 1 hour. The reaction mixture was then diluted with 15 ml ether and washed with two 5 ml portions of 1N HCl and 5 ml of water. The organic layer was dried over anhydrous MgSO$_4$ and concentrated. The residue was purified on a silica gel column, with 40% EtOAc/hexanes as eluting solvents, to give 180 mg of title compound as a white solid.

E.
[1S-[1α,2β(5Z),3β(1E,3R,4S),4α]]-N-Hydroxy-7-[3-(3-hydroxy-4-phenyl-1-pentenyl)-7-oxabicyclo[2.2.1]hept-2-yl]-5-heptenamide To a solution of 126 mg of Part D compound (0.21 mmole) in 1.5 ml of tetrahydrofuran at 25° C. was added 500 μl of a 2N HCl solution. After stirring at 25° C. for 6 hours, the mixture was neutralized by addition of solid NaHCO$_3$. The layers were separated and the aqueous layer was extracted with three 5 ml portions of CH$_2$Cl$_2$. The combined organic layer was dired over anhydrous MgSO$_4$ and concentrated. The residue was purified on a silica gel column, with 50% EtOAc/hexanes→EtOAc as eluting solvents, to give 34 mg of title product.

TLC: silica gel, 10% MeOH/CH$_2$Cl$_2$; R$_f$~0.35.

Anal Calcd for C$_{24}$H$_{33}$NO$_4$; 0.2 H$_2$O: C, 69.06; H, 8.07; N, 3.37; Found: C, 69.06; H, 8.08; N, 3.11.

[α]$_D$ = +47.3°, c = 1.5 mg/ml MeOH.

EXAMPLE 2

[1S-[1α,2β(5Z),3β(1E,3R,4S),4α]]-N-Hydroxy-7-[3-(3-hydroxy-4-phenyl-1-pentenyl)-7-oxabicyclo[2.2.1]hept-2-yl]-N-methyl-5-heptenamide A.
[1α,2β(Z),3β(1E,4S),4α]-7-[3-(3-Tetrahydropyranyloxy-4-phenyl-1-pentenyl)-N-methyl-N-tetrahydropyranyloxy-7-oxabicyclo[2.2.1]hept-2-yl]-5-heptenamide To a slurry of 17 mg of prewashed sodium hydride (50% in mineral oil, 0.38 mmole, 1.1 equiv.) in 2 ml of dry THF at 0° C. under an argon atmosphere was added a solution of 200 mg of Example 1 Part D compound (0.35 mmole) in 1 ml of THF. After stirring at 0° C. for 1 hour, 200 μl of methyl iodide (excess) was added and the stirring was continued at 0° C. for 1.5 hours and at 25° C. for 20 hours. The reaction was then quenched with glacial acetic acid and stirred at 50° C. for 15 minutes. The mixture was diluted with 10 ml of ether and washed with 3 ml of saturated NaHCO$_3$ solution and 3 ml of H$_2$O. The organic layer was dried over anhydrous MgSO₄ and concentrated to give 187 mg of title compound as a yellow oil.

B.
[1S-[1α,2β(5Z),3β(1E,3R,4S),4α]]-N-Hydroxy-7-[3-(3-hydroxy-4-phenyl-1-pentenyl)-7-oxabicyclo[2.2.1]hept-2-yl]-N-methyl-5-heptenamide A mixture of 187 mg of Part A compound (0.32 mmole), 20 mg of Amberlyst-15 resins in 2 ml of methanol was stirred at 25° C. for 20 hours, then filtered through a bed of Celite. The solid was washed with 20 ml of ether. The combined filtrate was concentrated and the residue was purified on a CC-7 silica gel column, with a gradient of ether/hexanes as eluting solvents, to give 81 mg of title product as a clear oil.

TLC: silica gel; 10% MeOH/CH₂Cl₂; R_f~0.5.

Anal Calcd for C₂₅H₃₅NO₄: C, 72.60; H, 8.53; N, 3.38.

$[\alpha]_D = +71.8°$, c=1.6 mg/ml MeOH.

EXAMPLE 3

[1S-[1α,2β(5Z),3β(1E,3R,4S),4α]]-N-(2-Hydroxyphenyl)-7-[3-(3-hydroxy-4-phenyl-1-pentenyl)-7-oxoabicyclo[2.2.1]hept-2-yl]-5-heptenamide

A.
[1α,2β(Z),3β(1E,4S),4α]-7-[3-(3-Tetrahydropyranyloxy-4-phenyl-1-pentenyl)-N-(2-hydroxyphenyl)-7-oxabicyclo[2.2.1]hept-2-yl]-5-heptenamide To a solution of 40 mg of Example 1 Part C acid (85.4 μmole) in 0.4 ml of CH₂Cl₂ was added 14.4 mg of 1-hydroxybenzotriazole (102.4 μmole, 1.2 equiv.) and 20.8 mg of 1,3-dicyclohexylcarbodiimide (102.4 μmole, 1.2 equiv.). After stirring at 25° C. for 1 hour, 18.4 mg of 2-aminophenol (169.6 μmole, 2 equiv.) was added and the stirring was continued for 20 hours. The reaction mixture was then diluted with 10 ml of ether and washed with two 5 ml of 1N H₂O. The organic layer was dried over anhydrous MgSO₄ and concentrated. The residue was purified on a silica gel column, with 30% EtOAc/hexanes as eluting solvents, to yield 42 mg of title compound as a white foam.

B.
[1S-[1α,2β(5Z),3β(1E,3R,4S),4α]]-N-(2-Hydroxyphenyl)-7-[3-(3-hydroxy-4-phenyl-1-pentenyl)-7-oxabicyclo[2.2.1]hept-2-yl]-5-heptenamide A mixture of 78 mg of Part A compound (0.14 mmole) and 14 mg of Amberlyst-15 resin in 2 ml of methanol was stirred at 25° C. for 5 hours then filtered through a bed of Celite. The solid was washed with 10 ml of methanol. The combined filtrate was concentrated and the residue was purified on a silica gel column, with 30% EtOAc/hexanes as eluting solvents, to give 42 mg of title compound as a white foam.

TLC: silica gel; EtOAc/Hexane (1:1); R_f~0.6.

Anal Calcd for C₃₀H₃₇NO₄; 0.5 H₂O: C, 74.34; H, 7.90; N, 2.89; Found: C, 74.51; H, 7.89; N, 2.62.

$[\alpha]_D = +58.3°$, c=0.6 mg/ml MeOH

EXAMPLE 4

[1S-[1α,2β(5Z),3β(1E,3R,4S),4α]]-N-Methoxy-[3-(3-hydroxy-4-phenyl-1-pentenyl)-7-oxabicyclo[2.2.1]hept-2-yl]-5-heptenamide Following the procedure of Example 1 except substituting methoxyamine for tetrahydropyranyloxyamine, the title compound is obtained.

EXAMPLE 5

[1S-[1α,2β(5Z),3β(1E,3R,4S),4α]]-N-Methyl-N-(2-hydroxyphenyl)-[3-(3-hydroxy-4-phenyl-1-pentenyl)-7-oxabicyclo[2.2.1]hept-2-yl]-5-heptenamide Following the procedure of Example 3 except substituting N-methyl-2-aminophenol for 2-aminophenol, the title compound is obtained.

EXAMPLE 6

[1S-[1α,2β(5Z),3β(1E,3S,4S),4α]]-N-Ethoxy-N-ethyl-7-[3-(3-hydroxy-4-phenyl-1-pentenyl)-7-oxabicyclo[2.2.1]hept-2-yl]-5-heptenamide Following the procedure of Example 4 except substituting N-ethoxy-N-ethylamine for methoxyamine, the title compound is obtained.

EXAMPLE 7

[1S-[1α,2β(5Z),3β(1E,3R,4S),4α]]-N-Hydroxy-7-[3-(3-hydroxy-3-phenyl-1-propenyl)-7-oxabicyclo[2.2.1]-hept-2-yl]-5-heptenamide Following the procedure of Example 1 except substituting propionic acid for 2-phenylpropionic acid, the title compound is obtained.

EXAMPLE 8

[1S-[1α,2β(5Z),3β(1E,3R,4S),4α]]-N-Hydroxy-7-[3-(3-hydroxy-4-phenyl-1-butenyl)-7-oxabicyclo[2.2.1]-hept-2-yl]-5-heptenamide Following the procedure of Example 1 except substituting phenylacetic acid for 2-phenylpropionic acid, the title compound is obtained.

EXAMPLE 9

[1S-[1α,2β(5Z),3β(1E,3R,4S),4α]]-N-Hydroxy-7-[3-(3-hydroxy-3-cyclohexyl-1-propenyl)-7-oxabicyclo[2.2.1-]hept-2-yl]-N-methyl-5-heptenamide Following the procedure of Example 2 except substituting cyclohexyl carboxylic acid for 2-phenylpropionic acid, the title compound is obtained.

EXAMPLE 10

[1S-[1α,2β(5Z),3β(1E,3R,4S),4α]]-N-Ethyl-N-hydroxy-7-[3-(3-hydroxy-4-cyclopentyl-1-butenyl)-7-oxabicyclo[2.2.1]hept-2-yl]-5-heptenamide Following the procedure of Example 2 except substituting cyclopentylacetic acid for 2-phenylpropionic acid and ethyl iodide for methyl iodide, the title compound is obtained.

EXAMPLE 11

[1S-[1α,2β(5Z),3β(1E,3R,4S),4α]]-N-Hydroxy-N-propyl-7-[3-(3-hydroxy-1,5-hexadienyl)-7-oxabicyclo[2.2.1-]hept-2-yl]-5-heptenamide Following the procedure of Example 2 except substituting 2-propenyl carboxylic acid for 2-phenylpropionic acid and propyl iodide for methyl iodide, the title compound is obtained.

EXAMPLE 12

[1S-[1α,2β(5Z),3β(1E,3R,4S),4α]]-N-(3-Hydroxyphenyl)-7-[3-(3-hydroxy-1-nonenyl)-7-oxabicyclo[2.2.1]hept-2-yl]-5-heptenamide Following the procedure of Example 3 except substituting hexane carboxylic acid for 2-phenylpropionic acid and 3-aminophenol for 2-aminophenol, the title compound is obtained.

EXAMPLE 13

[1S-[1α,2β(5Z),3β(1E,3R,4S),4α]]-N-(4-Hydroxyphenyl)-N-propyl-7-[3-(3-hydroxy-1-pentenyl)-7-oxabicyclo[2.2.1]hept-2-yl]-5-heptenamide Following the procedure of Example 5 except substituting propionic acid for 2-phenylpropionic acid and N-propyl-4-aminophenol for N-methyl-2-aminophenol, the title compound is obtained.

EXAMPLE 14

[1S-[1α,2β(5Z),3β(1E,3R,4S),4α]]-N-Hydroxy-7-[3-(3-hydroxy-3-phenyl-1-propenyl)-7-oxabicyclo[2.2.1]hept-2-yl]-5-heptenamide Following the procedure of Example 1 except substituting benzoic acid for 2-phenylpropionic acid, the title compound is obtained.

EXAMPLE 15

[1S-[1α,2β(5Z),3β(1E,3R,4S),4α]]-N-Hydroxy-7-[3-(3-hydroxy-3-cyclohexyl-1-propenyl)-7-oxabicyclo[2.2.1]hept-2-yl]-5-heptenamide Following the procedure of Example 1 except substituting cyclohexylcarboxylic acid for 2-phenylpropionic acid, the title compound is obtained.

EXAMPLE 16

[1S-[1α,2β(5Z),3β(1E,3R,4S),4α]]-N-Hydroxy-7-[3-(3-hydroxy-4-cyclopentyl-1-butenyl)-7-oxabicyclo[2.2.1]hept-2-yl]-5-heptenamide Following the procedure of Example 1 except substituting cyclopentylacetic acid for 2-phenylpropionic acid, the title compound is obtained.

EXAMPLE 17

[1S-[1α,2β(5Z),3β(1E,3R,4S),4α]]-N-Butyl-N-hydroxy-[3-(3-hydroxy-1,6-heptadienyl)-7-oxabicyclo[2.2.1]-hept-2-yl]-5-heptenamide Following the procedure of Example 1 except substituting 3-butenyl carboxylic acid for 2-phenylpropionic acid and butyl iodide for methyl iodide, the title compound is obtained.

EXAMPLE 18

[1S-[1α,2β(5Z),3β(1E,3R,4S),4α]]-N-(2-Hydroxyphenyl)-7-[3-(3-hydroxy-1-phenyl)-7-oxabicyclo[2.2.1]hept-2-yl]-5-heptenamide Following the procedure of Example 3 except substituting propionic acid for 2-phenylpropionic acid, the title compound is obtained.

EXAMPLE 19

[1α,2β(5Z),3β(3R,4S),4α]-N-Hydroxy-7-[3-(3-Hydroxy-4-phenyl-1-pentyl)-7-oxabicyclo(2.2.1]hept-2-yl]-5-heptenamide

A.

[1S-[1α,2β(Z),3β(4S),4α]]-7-[3-(3-Oxo-4-phenyl-1-pentyl)-7-oxabicyclo[2.2.1]-hept-2-yl]-5-heptenoic acid, methyl ester To a suspension of 686 mg of purified cuprous bromide (4.8 mmole) in 12 ml of dry THF, cooled at 0°–5° C. was added with stirring 1.35 ml of a 3.5M solution of red-Al (sodium bis(2-methoxyethoxy)aluminumhydride) in toluene dropwise. The solution was stirred at 0°–5° C. for 30 minutes, whereupon it was cooled to −78° C. and 2 ml of n-butanol (18 mmole) was added rapidly, followed by a solution of 476 mg of Example 1 Part A (3) enone (1.2 mmole) in 4 ml of dry THF. After 10 minutes at −78° C., the reaction mixture was warmed to −20° C. and left for an additional one hour. The reaction mixture was quenched by addition of 70 ml of water and then poured into saturated ammonium chloride solution and was extracted with ether (x3). The ether extract was dried over anhydrous magnesium sulfate, filtered and the filtrate was concentrated under reduced pressure. 480 Mg of desired title ketone was obtained (100% yield) as a colorless oil.

B.

[1S-[1α,2β(Z),3β(3R,4S),4α]]-7-[3-(3-Hydroxy-4-phenyl-1-pentyl)-7-oxabicyclo[2.2.1]hept-2-yl]-5-heptenoic acid, methyl ester To a solution of 400 mg of title A ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 40 mg of solid sodium borohydride (~1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous hydrochloric acid solution. The ether extract is dried over anhydrous MgSO4 and concentrated under reduced pressure. The crude residue is chromatographed on a silica gel column and eluted with 30–50% ethyl acetate in hexane to obtain the desired title 3R-alcohol.

C.

[1α,2β(5Z),3β(3R,4S),4α]-N-Hydroxy-7-[3-(3-Hydroxy-4-phenyl-1-pentyl)-7-oxabicyclo[2.2.1]hept-2-yl]-5-heptenamide Following the procedure of Example 1 except substituting the Part B alcohol for the Example 1 Part A alcohol, the title compound is obtained.

EXAMPLE 20

[1S-[1α,2β(5Z),3β(4S),4α]]-N-Hydroxy-7-[3-(3-Hydroxy-3-phenyl-1-propyl)-7-oxabicyclo[2.2.1]-hept-2-yl]-5-heptenamide Following the procedure of Example 19 and Example 1 except substituting benzoic acid for 2-phenylpropionic acid, the title compound is obtained.

EXAMPLE 21

[1S-[1α,2β(5Z),3β(4S),4α]]-N-Hydroxy-7-[3-(3-Hydroxy-4-phenyl-1-butyl)-7-oxabicyclo[2.2.1]-hept-2-yl]-5-heptenamide Following the procedure of Example 19 and Example 1 except substituting phenylacetic acid for 2-phenylpropionic acid, the title compound is obtained.

EXAMPLE 22

[1S-[1α,2β(5Z),3β(4S),4α]]-N-Hydroxy-7-[3-(3-hydroxy-3-cyclohexyl-1-propyl)-7-oxabicyclo[2.2.1]hept-2-yl]-N-methyl-5-heptenamide Following the procedure of Example 19 and Example 2 except substituting cyclohexylcarboxylic acid for 2-phenylpropionic acid, the title compound is obtained.

EXAMPLE 23

[1S-[1α,2β(5Z),3β(4S),4α]]-N-Ethyl-N-hydroxy-7-[3-(3-hydroxy-4-cyclopentyl-1-butyl)-7-oxabicyclo[2.2.1]hept-2-yl]-5-heptenamide Following the procedure of Examples 19 and 2 except substituting cyclopentylacetic acid for 2-phenylpropionic acid and ethyl iodide for methyl iodide, the title compound is obtained.

EXAMPLE 24

[1S-[1α,2β(5Z),3β(4S),4α]]-N-Hydroxy-N-propyl-7-[3-(3-hydroxy-5-hexenyl)-7-oxabicyclo[2.2.1]hept-2-yl]-2-butenyl]-5-heptenamide Following the procedure of Example 19 and Example 2 except substituting 2-propenyl carboxylic acid for 2-phenylpropionic acid and propyl iodide for methyl iodide, the title compound is obtained.

EXAMPLE 25

[1S-[1α,2β(5Z),3β(4S),4α]]-N-(3-Hydroxyphenyl)-7-[3-(3-hydroxy-1-nonyl)-7-oxabicyclo[2.2.1]hept-2-yl]-5-heptenamide Following the procedure of Example 19 and Example 3 except substituting hexanecarboxylic acid for 2-phenylpropionic acid and 3-aminophenol for 2-aminophenol, the title compound is obtained.

EXAMPLE 26

[1S-[1α,2β(2E,5Z),3β(4S),4α]]-N-(4-Hydroxyphenyl-N-propyl-7-[3-(3-Hydroxy-3-phenyl-1-propyl)-7-oxabicyclo[2.2.1]hept-2-yl]-5-heptenamide Following the procedure of Examples 19 and 5 except substituting propionic acid for 2-phenylpropionic acid and N-propyl-4-aminophenol for N-methyl-2-aminophenol, the title compound is obtained.

EXAMPLES 27 TO 36

Following the procedure of Example 2 (where B is CH=CH) or Example 19 (where B is (CH₂)₂), except substituting for 2-phenylpropionic acid, the compound shown in Column I of Table I set out below, substituting for carbomethoxymethylenetriphenylphosphorane, the compound shown in Column II and substituting for methyl iodide, the compound shown in Column III, the compound of the invention shown in Column IV is obtained.

TABLE I

| | | | | | | Column IV |
| | | | | | |  |

| Ex. No. | Column I R³—COOCH₃ R³ | Column II (C₆H₅)₃P=CH(CH₂)$_{m-1}$—COOCH₃ m | Column III R¹Hal | A | m | R¹ | R³ |
|---|---|---|---|---|---|---|---|
| 27. | CH₃ | 2 | CH₃ | CH=CH | 2 | CH₃ | CH₃ |
| 28. | C₆H₅ | 3 | C₂H₅I | (CH₂)₂ | 3 | C₂H₅ | C₆H₅ |
| 29. | C₆H₅CH₂ | 3 | C₃H₇Br | CH=CH | 3 | C₃H₇ | C₆H₅CH₂ |
| 30. |  | 4 | C₄H₉I | (CH₂)₂ | 4 | C₄H₉ | 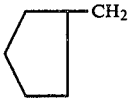 |
| 31. |  | 4 | C₅H₁₁Br | CH=CH | 4 | C₅H₁₁ |  |
| 32. | CH₃CH=CH— | 5 | C₂H₅Br | (CH₂)₂ | 5 | C₂H₅ | CH₃—CH=CH— |
| 33. | C₂H₅ | 1 | C₃H₇I | CH=CH | 1 | C₃H₇ | C₂H₅ |
| 34. | C₆H₄(CH₂)₂ | 1 | C₄H₉I | (CH₂)₂ | 1 | C₄H₉ | C₆H₄(CH₂)₂ |
| 35. |  | 2 | CH₃Cl | CH=CH | 2 | CH₃ |  |
| 36. | CH₃CH₂—CH=CH— | 3 | C₂H₅I | (CH₂)₂ | 3 | C₂H₅ | CH₃CH₂—CH=CH— |

EXAMPLES 37 TO 46

Following the procedure of Example 3 (where B is CH=CH), Examples 19 and 3 (where B is (CH$_2$)$_2$), except substituting for 2-phenylpropionic acid, the compound shown in Column I of Table II set out below substituting for carbomethoxymethylenetriphenylphosphorane, the compound shown in Column II, and substituting for 2-aminophenol, the compound shown in Column III, the compound of the invention shown in Column IV is obtained.

TABLE II

| | Column I | Column II | Column III |
|---|---|---|---|
| | R$^3$—COOCH$_3$ | (C$_6$H$_5$)$_3$P=CH—(CH$_2$)$_{m-1}$—CO$_2$CH$_3$ |  |

| Ex. No. | R$^3$ | m | NH (OH position)<br>$\vert$<br>R$^1$ |
|---|---|---|---|
| 37. | CH$_3$ | 2 | NHCH$_3$ (2) |
| 38. | C$_6$H$_5$ | 3 | NHCH$_3$ (3) |
| 39. | C$_6$H$_5$CH$_2$ | 3 | NHC$_2$H$_5$ (4) |
| 40. |  | 4 | NHCH$_2$H$_5$ (3) |
| 41. | 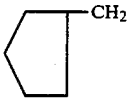 | 4 | NHC$_3$H$_7$ (2) |
| 42. | CH$_3$CH=CH— | 5 | NHC$_3$H$_7$ (2) |
| 43. | C$_2$H$_5$ | 1 | NHC$_4$H$_9$ (3) |
| 44. | C$_6$H$_4$(CH$_2$)$_2$ | 1 | NHC$_5$H$_{11}$ (4) |
| 45. |  | 2 | NHCH$_3$ (3) |
| 46. | CH$_3$CH$_2$—CH=CH— | 3 | NHC$_2$H$_5$ (2) |

Column IV

| Ex. No. | A | m | N—R$^1$ (OH position) | R$^3$ |
|---|---|---|---|---|
| 37. | CH=CH | 2 | CH$_3$ (2) | CH$_3$ |
| 38. | (CH$_2$)$_2$ | 3 | CH$_3$ (3) | C$_6$H$_5$ |
| 39. | CH=CH | 3 | C$_2$H$_5$ (4) | C$_6$H$_5$CH$_2$ |
| 40. | (CH$_2$)$_2$ | 4 | C$_2$H$_5$ (3) | 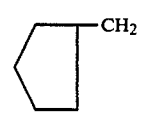 |
| 41. | CH=CH | 4 | C$_3$H$_7$ (2) | |
| 42. | (CH$_2$)$_2$ | 5 | C$_3$H$_7$ (2) | CH$_3$—CH=CH— |
| 43. | CH=CH | 1 | C$_4$H$_9$ (3) | C$_2$H$_5$ |
| 44. | (CH$_2$)$_2$ | 1 | C$_5$H$_{11}$ (4) | C$_6$H$_4$(CH$_2$)$_2$ |

TABLE II-continued

| | | | | |
|---|---|---|---|---|
| 45. | CH=CH | 2 | CH₃ (3) |  |
| 46. | (CH₂)₂ | 3 | C₂H₅ (2) | CH₃CH₂—CH=CH— |

What is claimed is:

1. A compound having the structural formula

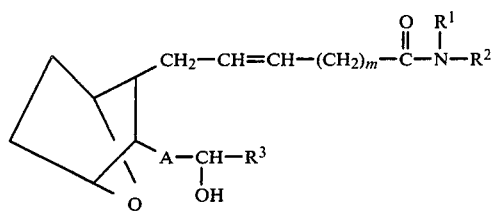

and including all stereoisomers thereof;
wherein m is 1 to 5; A is —CH=CH— or (CH₂)₂; R¹ is hydrogen or lower alkyl, R² is hydroxy, alkoxy or hydroxyphenyl; and R³ is lower alkyl, aryl, aralkyl, cycloalkyl, cycloalkylalkyl, lower alkenyl containing 2 to 12 carbons or lower alkynyl containing 2 to 12 carbons, wherein lower alkyl or alkyl alone or as part of another group contains 1 to 12 carbons and is unsubstituted or is substituted with halo, hydroxy, alkylamino, alkanoylamino, nitro, cyano, thiol, alkylthio, CF₃, alkoxy, aryl, alkyl-aryl, haloaryl, cycloalkyl or alkylcycloalkyl; aryl alone or as part of another group contains 6 to 10 carbons in the ring portion and is unsubstituted or is substituted with 1 or 2 lower alkyl groups, 1 or 2 halogens, 1 or 2 hydroxy groups, 1 or 2 lower alkoxy groups, 1 or 2 nitro groups, 1 or 2 cyano groups, 1 or 2 thiol groups, and/or 1 or 2 alkylthio groups, or 1 or 2 NR²R³ groups or 1 or 2

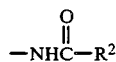

groups wherein R² and R³ are independently H, lower alkyl or aryl;
cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups; and
(CH₂)ₘ may contain 1 or 2 lower alkyl and/or halo substituents.

2. The compound as defined in claim 1 wherein A is —CH=CH—.

3. The compound as defined in claim 2 wherein R¹ is H or methyl, R² is hydroxy or 2-hydroxyphenyl, and R³ is butyl, pentyl, hexyl, heptyl, 1,1-dimethylpentyl or benzyl-methyl.

4. The compound as defined in claim 1 having the name [1S-[1α,2β(5Z),3β(1E,3R,4S),4α]]-N-hydroxy-7-[3-(3-hydroxy-4-phenyl-1-pentenyl)-7-oxabicyclo[2.2.1]hept-2-yl]-N-methyl-5-heptenamide including all stereoisomers thereof.

5. The compound as defined in claim 1 having the name [1S-[1α,2β(5Z),3β(1E,3R,4S),4α]]-N-hydroxy-7-[3-(3-hydroxy-4-phenyl-1-pentenyl)-7-oxabicyclo[2.2.1]hept-2-yl]-5-heptenamide.

6. The compound as defined in claim 1 having the name [1S-[1α,2β(5Z),3β(1E,3R,4S),4α]]-N-(2-hydroxyphenyl)-7-[3-(3-hydroxy-4-phenyl-1-pentenyl)-7-oxabicyclo[2.2.1]hept-2-yl]-5-heptenamide including all stereoisomers thereof.

7. A method of inhibiting arachidonic acid-induced platelet aggregation and bronchoconstriction or inhibiting Δ⁵-lipoxygenase, which comprises administering to the circulatory system of a mammalian host an effective amount of a compound as defined in claim 1 or a pharmaceutically acceptable salt thereof.

8. The method as defined in claim 7 wherein said compound is administered in an amount within the range of from about 1 to about 100 mg/kg.

9. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

10. A method of inhibiting bronchoconstriction associated with asthma, inhibiting or reducing inflammation or inhibiting psoriasis, which comprises administering to a mammalian host an effective amount of a compound as defined in claim 1 or a pharmaceutically acceptable salt thereof.

11. A method for treating peripheral vascular disease, which comprises topically or systemically administering to a mammalian host an effective amount of a compound as defined in claim 1 or a pharmaceutically acceptable salt thereof.

12. The method as defined in claim 10 wherein said compound is administered in an amount within the range of from about 1 to about 100 mg/kg.

* * * * *

UNITED STATES PATENT AND TRADEMARK OFFICE
CERTIFICATE OF CORRECTION

PATENT NO. :  4,611,007
DATED       :  September 9, 1986
INVENTOR(S) :  Jagabandhu Das It is certified that error appears in the above-identified patent and that said Letters Patent is hereby corrected as shown below:

Column 1, line 43, "alkylthiohalo" should read
  --alkylthio; halo--.
Column 1, line 63, "phenyl naphthyl" should read --phenyl or
  naphthyl--.
Column 5, line 16, "lowr" should read --lower--.
Column 10, lines 31 to 38, structure "Ib" should read

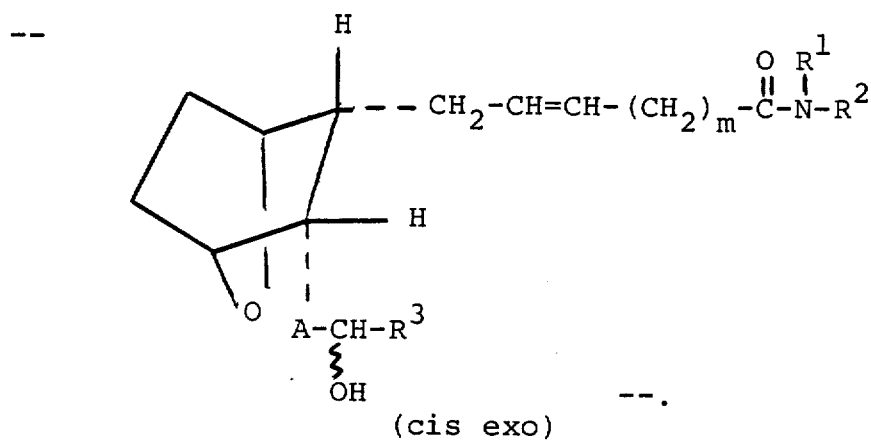

(cis exo)

Signed and Sealed this

Thirtieth Day of December, 1986

Attest:

DONALD J. QUIGG

Attesting Officer          Commissioner of Patents and Trademarks